United States Patent
Li et al.

(10) Patent No.: US 9,630,969 B2
(45) Date of Patent: Apr. 25, 2017

(54) N-ALKYL TRYPTANTHRIN DERIVATIVE, PREPARATION METHOD FOR SAME, AND APPLICATION THEREOF

(71) Applicant: SHANGHAI TIN TSZ BIO VALLEY BIOLOGICAL ENGINEERING CO., LTD, Pudong New Area Shanghai (CN)

(72) Inventors: Hanpu Li, Pudong New Area Shanghai (CN); Chunxiang Kuang, Pudong New Area Shanghai (CN); Jianzhi Li, Pudong New Area Shanghai (CN)

(73) Assignee: SHANGHAI TIN TSZ BIO VALLEY BIOLOGICAL ENGINEERING CO., LTD, Pudong New Area Shanghai (CN)

(*) Notice: Subject to any disclaimer, the term of this patent is extended or adjusted under 35 U.S.C. 154(b) by 0 days.

(21) Appl. No.: 14/905,563

(22) PCT Filed: Jul. 25, 2014

(86) PCT No.: PCT/CN2014/083030
§ 371 (c)(1),
(2) Date: Jan. 15, 2016

(87) PCT Pub. No.: WO2015/007249
PCT Pub. Date: Jan. 22, 2015

(65) Prior Publication Data
US 2016/0168152 A1    Jun. 16, 2016

(30) Foreign Application Priority Data

Jul. 15, 2013   (CN) .......................... 2013 1 0295743

(51) Int. Cl.
*A61K 31/50* (2006.01)
*C07D 487/04* (2006.01)

(52) U.S. Cl.
CPC .................. *C07D 487/04* (2013.01)

(58) Field of Classification Search
USPC .......................... 514/250, 253; 544/246, 247
See application file for complete search history.

(56) References Cited

U.S. PATENT DOCUMENTS

| 5,441,955 A * | 8/1995 | Baker ................ C07D 471/14 514/2.4 |
| 6,531,487 B2 * | 3/2003 | Pitzer .................. C07D 471/14 514/152 |
| 2004/0241192 A1 * | 12/2004 | Valiante ............... A61K 31/498 424/204.1 |

FOREIGN PATENT DOCUMENTS

| CA | 2369448 A1 | 10/2000 |
| CN | 102579452 A | 7/2012 |
| CN | 103570726 A | 2/2014 |
| CN | 103570727 A | 2/2014 |
| JP | 2010248086 A | 11/2010 |
| WO | 9513807 A1 | 5/1995 |
| WO | 0018769 A2 | 4/2000 |
| WO | 2004064759 A2 | 8/2004 |

OTHER PUBLICATIONS

Liu et al. CAS: 149: 32323, 2008.*
Kawakami's CAS: 153: 580336, 2010.*
Nichols et al. CAS: 139: 191372, 2003.*
Bhattacharjee et al. CAS: 137: 210404, 2002.*
Hamburger et al. CAS: 133: 305580, 2000.*
International Seach Report issued Oct. 22, 2014 in International Application No. PCT/CN2014/083030.
MacKenzie et al., "Role of Indoleamine 2,3-Dioxygenase in Antimicrobial Defence and Immuno-Regulation: Tryptophan Depletion Versus Production of Toxic Kynurenines," Current Drug Metabolism, vol. 8, pp. 237-244 (2007).

* cited by examiner

*Primary Examiner* — Rei-Tsang Shiao
(74) *Attorney, Agent, or Firm* — Panitch Schwarze Belisario & Nadel LLP

(57) ABSTRACT

An N-alkyl tryptanthrin derivative, a preparation method for same, and an application thereof are provided. The structure of the derivative is as represented by formula I. The N-alkyl tryptanthrin derivative can serve as a highly active IDO inhibitor, for use in preparing a medicament for prevention and/or treatment of a disease having a pathological characteristic of an IDO-mediated tryptophan metabolic pathway.

11 Claims, No Drawings

N-ALKYL TRYPTANTHRIN DERIVATIVE, PREPARATION METHOD FOR SAME, AND APPLICATION THEREOF

CROSS-REFERENCE TO RELATED APPLICATION

This application is a Section 371 of International Application No. PCT/CN2014/083030, filed Jul. 25, 2014, which was published in the Chinese language on Jan. 22, 2015, under International Publication No. WO 2015/007249 A1, and the disclosure of which is incorporated herein by reference.

FIELD OF THE INVENTION

The present invention relates to the field of medicinal chemistry. Specifically, the present invention relates to a type of n-alkyl tryptanthrin derivative, the preparation method for same, and the application thereof.

BACKGROUND OF THE INVENTION

Indoleamine 2,3-dioxygenase (IDO) is an intracellular enzyme containing heme, which is the only rate-limiting enzyme outside the liver that can catalyze tryptophan metabolism to produce a series of metabolites including quinoline acid along kynurenine pathway (MacKenzie et al. Current Drug Metabolism, 2007, 8:237-244). Since 1990s, the important roles that played by indoleamine 2, 3-dioxygenase and the kynurenine pathway (KP) by which it catalyzes the tryptophan metabolism in a variety of disease processes has attracted increasing attentions.

Indoleamine 2,3-dioxygenase IDO catalyzes the oxidation reaction in which the essential amino acids—amino acids are converted into N-formyl-kynurenine by dioxygen, and is responsible for cleaning up the tryptophan in the human body. IDO causes tryptophan lacking in vivo microenvironment by degrading tryptophan, and then leads to the occurrence of diseases closely related to the lack of tryptophan such as cancer, cataracts, and nerve disorders. Therefore, searching of efficient IDO target-based inhibitor has become a hot topic in medicinal development in recent years.

Tryptanthrin is a quinoline indole alkaloids, of which the chemical name is indole [2,1-b] quinazoline-6,12-dione, and it is a yellow needle crystal which mainly exists in the *Baphicacanthus cusia, Polygonum tinctorium, Isatis tinctoria* and other Indigo producing plants. Meanwhile, tryptanthrin can also be extracted from the microorganism fermentation broth. In recent years, domestic and foreign scholars have partially researched the pharmacology of tryptophan, of which the effects mainly show in anti-bacterial, anti-inflammatory, anti-tumor and anti-parasitic aspects, etc. It has been shown that tryptanthrin is a very scarce medicinal resource with good potentials in research and development for new drugs. However, the development of tryptanthrin compounds is insufficient, and there is still a need in the art to further develop highly effective tryptanthrin derivatives of novel structure.

SUMMARY OF THE INVENTION

The object of the present invention is to provide a type of highly effective tryptanthrin derivatives with novel structure, the preparation method for same, and applications thereof.

In the first aspect of the present invention, it provides a compound of formula I, or a pharmaceutically acceptable salt thereof:

![Formula I structure]

Wherein Z is none or F;

$T_1$ and $T_2$ are independently H, substituted or unsubstituted $C_1$-$C_3$ alkyl, substituted or unsubstituted $C_1$-$C_3$ alkoxy, halogen or

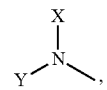

and at least one of $T_1$ and $T_2$ is

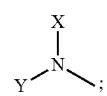

X and Y are independently selected from: H, substituted or unsubstituted $C_1$-$C_5$ alkyl, substituted or unsubstituted $C_2$-$C_5$ alkenyl, substituted or unsubstituted $C_1$-$C_5$ halogenated alkyl; or, X and Y are independently selected from: substituted or unsubstituted $C_1$-$C_5$ alkylene, substituted or unsubstituted $C_2$-$C_5$ alkenylene, substituted or unsubstituted $C_1$-$C_5$ halogenated alkylene, and X and Y are linked by —$CH_2$—, —O—, or —N(Ra)Rb—, wherein Ra is H or substituted or unsubstituted $C_1$-$C_3$ alkyl, while Rb is none, substituted or unsubstituted $C_1$-$C_3$ methylene;

the substituted means substituted by substitutional groups selected from the following group: $C_1$-$C_5$ alkyl, $C_2$-$C_5$ alkenyl, $C_1$-$C_5$ alkoxy, trifluoromethyl, halogen, amidogen and nitro.

In another preferred embodiment, Z is F.

In another preferred embodiment, X is substituted or unsubstituted $C_1$-$C_3$ alkyl, Y is substituted or unsubstituted $C_1$-$C_3$ alkyl.

In another preferred embodiment, in the formula, X, Y together with the adjacent N form the following structures:

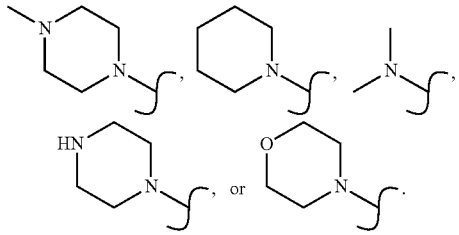

In another preferred embodiment, the compound of formula I is one of the following compounds:

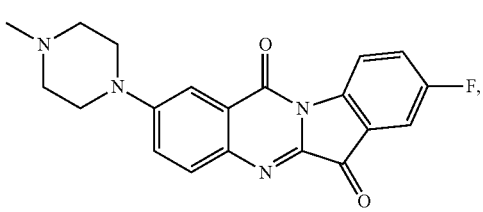

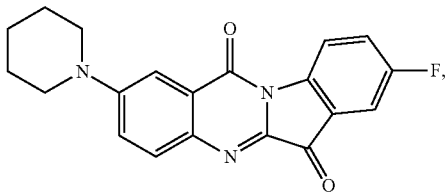

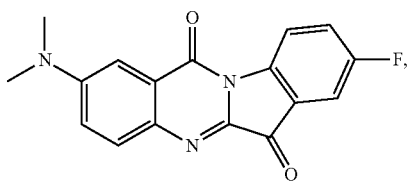

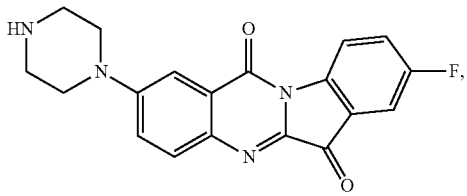

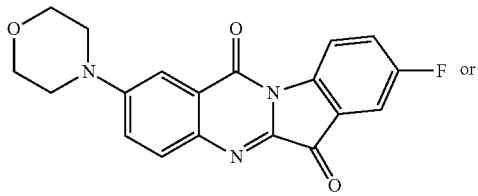

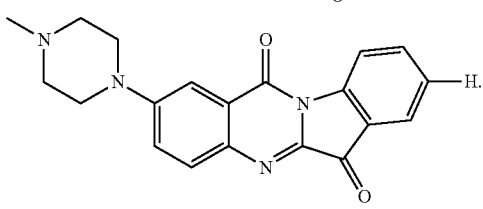

In the second aspect of the present invention, it provides a method of preparing the compound of formula I, which comprises the following steps:

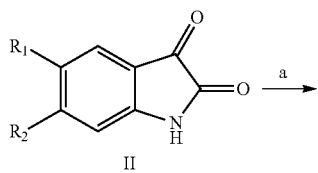

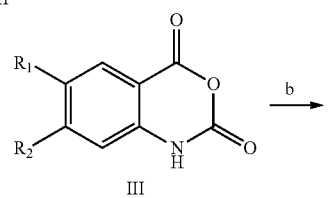

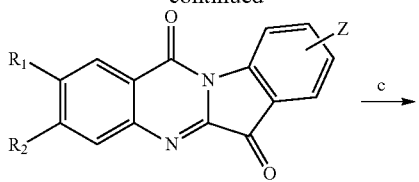

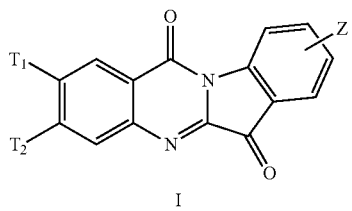

(a) oxidizing the compound of formula II to form the compound of formula III;

(b) reacting the compound of formula III with fluoric isatin or isatin so as to form the compound of formula IV; and (c) substituting the compound of formula IV so as to form the compound of formula I;

Wherein in each formula, $R_1$ and $R_2$ are independently selected from: H, Br or I, and $R_1$, $R_2$ are not simultaneously H;

$T_1$, $T_2$ and Z are as defined in the first aspect of the present invention.

In the third aspect of the present invention, it provides a use of the compound of formula I in the first aspect of the present invention or a pharmaceutically acceptable salt thereof, wherein in (i) the preparation of IDO inhibitor; or (ii) the preparation of drugs for the treatment of tryptophan metabolism disorder related diseases.

In another preferred embodiment, the compound of formula I is:

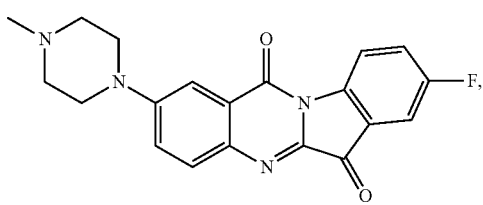

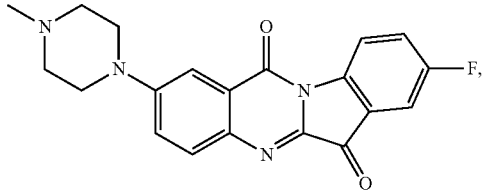

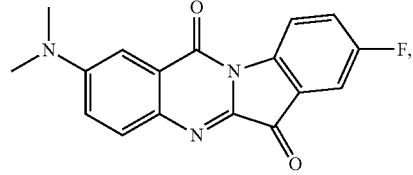

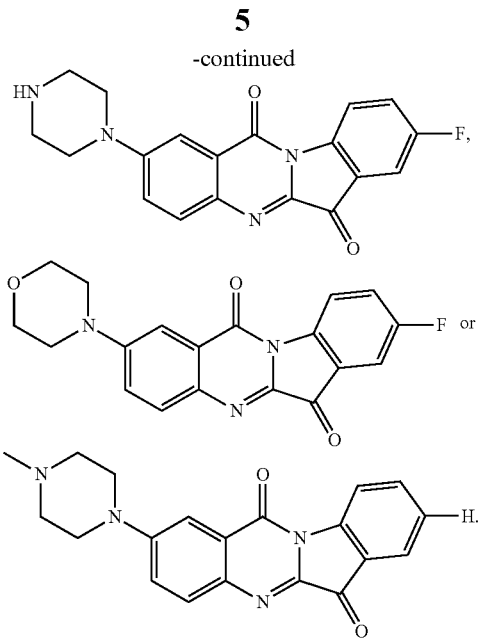

In another preferred embodiment, the diseases related to tryptophan metabolism disorder are selected from: cancer, Alzheimer's disease, cataracts, depression, anxiety disorders, AIDS, autoimmune diseases and mental disorders.

In the fourth aspect of the present invention, it provides a pharmaceutical composition which comprises:

the compound of formula I of the first aspect of the present invention or a pharmaceutically acceptable salt thereof; and a pharmaceutically acceptable carrier.

The tryptamine derivatives of the present invention can be used as IDO inhibitors of high activity for IDO-mediated diseases with pathological features in tryptophan metabolic pathway, including tumors, cancer, alzheimer's disease, autoimmune diseases, cataracts, mental disorders, depression, anxiety disorders, AIDS and other serious diseases. The tryptamine derivatives are very scarce medicinal resources with good potentials of research and development for new drugs.

It should be understood that, in the present invention, each of the technical features specifically described above and below (such as those in the Examples) can be combined with each other, thereby constituting new or preferred technical solutions which need not be specified again herein.

EMBODIMENTS FOR CARRYING OUT THE INVENTION

Through research, the inventor has unexpectedly discovered a type of tryptanthrin derivative with completely new structure as well as high IDO inhibitory activity. It can be used in the preparation of drugs for preventing and/or treating IDO-mediated diseases with pathological features in tryptophan metabolic pathway. The present invention is completed on this basis.

Compound of Formula I

As used herein, "N-alkyl tryptanthrin derivative of the present invention", "Compound of Formula I", "Compound shown in the Formula I", and "Compound as shown in the Formula I" can be used interchangeably, which all refer to the N-alkyl tryptanthrin derivative with the structure shown as the Formula I:

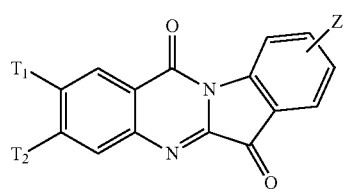 (I)

Wherein Z is none or F;

$T_1$ and $T_2$ are independently H, substituted or unsubstituted $C_1$-$C_3$ alkyl, substituted or unsubstituted $C_1$-$C_3$ alkoxy, halogen or

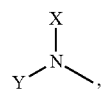, and at least one of $T_1$ and $T_2$ is

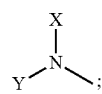;

X and Y are independently selected from: H, substituted or unsubstituted $C_1$-$C_5$ alkyl, substituted or unsubstituted $C_2$-$C_5$ alkenyl, substituted or unsubstituted $C_1$-$C_5$ halogenated alkyl; or, X and Y are independently selected from: substituted or unsubstituted $C_1$-$C_5$ alkylene, substituted or unsubstituted $C_2$-$C_5$ alkenylene, substituted or unsubstituted $C_1$-$C_5$ halogenated alkylene, and X and Y are linked by —CH$_2$—, —O—, or —N(Ra)Rb—, wherein Ra is H, or substituted or unsubstituted $C_1$-$C_3$ alkyl, while Rb is none, substituted or unsubstituted $C_1$-$C_3$ methylene;

The substituted means substituted by substitutional groups selected from the following group: $C_1$-$C_5$ alkyl, $C_2$-$C_5$ alkenyl, $C_1$-$C_5$ alkoxy, trifluoromethyl, halogen, amidogen and nitro.

In another preferred embodiment, X is substituted or unsubstituted $C_1$-$C_3$ alkyl, Y is substituted or unsubstituted $C_1$-$C_3$ alkyl.

In another preferred embodiment, X, Y and the adjacent N together form the following structures:

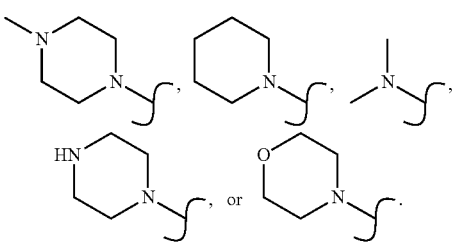

In another preferred embodiment, wherein X and Y are not H, or are not simultaneously H.

In another preferred embodiment, —N(Ra)Rb— is —NH—, —NH—CH$_2$— or —N(CH$_3$)—.

The substituted means having 1-5 substitutional groups, preferably, having one, two, or three substitutional groups.

In another preferred embodiment, Z is F.

Z is on the 7 position, the 8 position, the 9 position or the 10 position, preferably, Z is the 7 position or the 8 position.

In another preferred embodiment, the 8 position is F or H.

In the present invention, the numbering sequence of the compound of formula I is as follows:

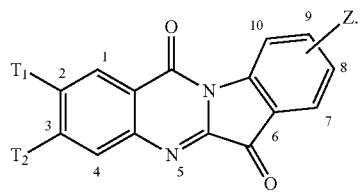

Preferably, the compound of formula I is:

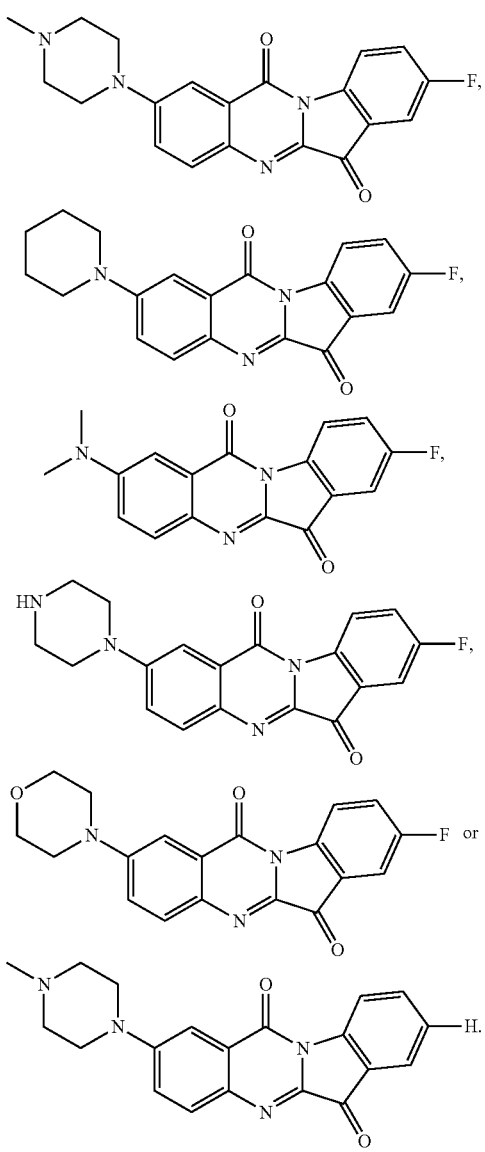

Preparation Method

A method of preparing the compound of formula I comprises:

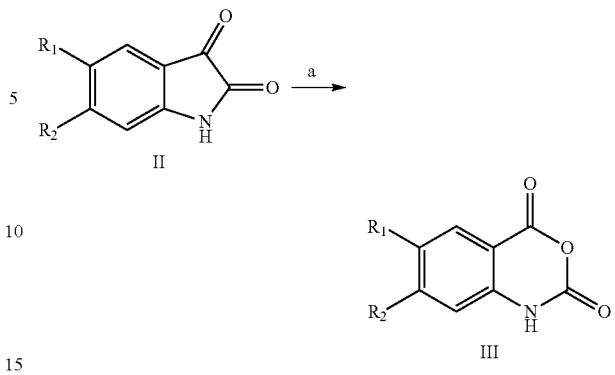

(a) oxidizing the compound of formula II to form the compound of formula III;

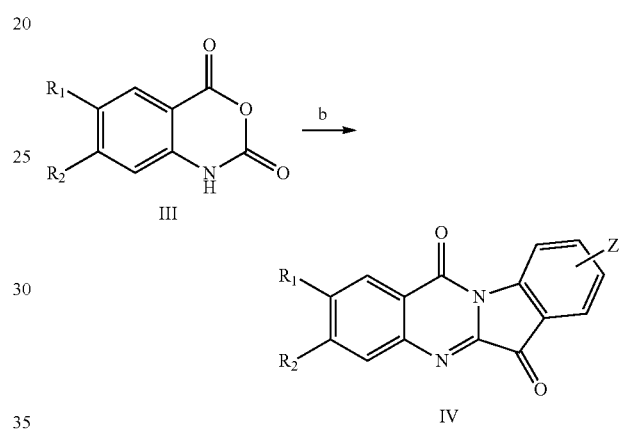

(b) reacting the compound of formula III with fluoric isatin or isatin so as to form the compound of formula IV; and

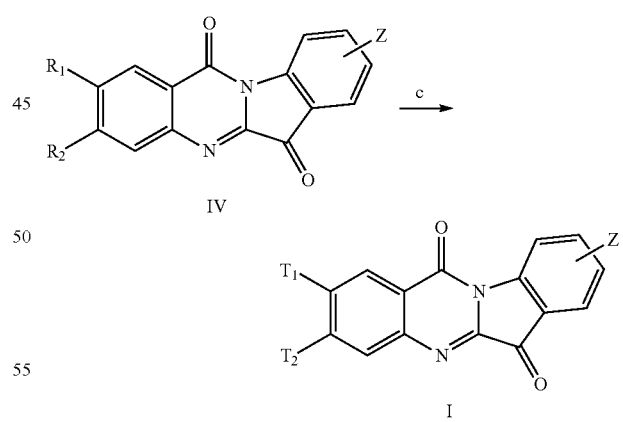

(c) substituting the compound of formula IV so as to form the compound of formula I;

Wherein in each formula, $R_1$ and $R_2$ are independently selected from: H, Br or I, and $R_1$, $R_2$ are not H simultaneously;

$T_1$, $T_2$ and Z are as mentioned above.

Generally, in the step a), in the organic solvent, the compound of formula III is obtained by oxidizing the compound of formula II for 2-3 hours with the presence of oxidizer under 20° C.-30° C. Preferably, the organic solvent is selected from dichloromethane, tetrahydrofuran, methanol, ethanol, 1,4-dioxane, toluene, acetonitrile, isopropanol, n-propanol and acetic acid; preferably, the oxidizer is selected from hydrogen peroxide, m-chloroperbenzoic acid, peracetic acid and perbenzoic acid. The feeding molar ratio of compound II and the oxidizer is 1:2-5; preferably, the feeding molar ratio is 1:2-3.

In the step b), the compound of formula III reacts with fluoro isatin or isatin with the presence of alkaline catalyst in the organic solvent, to provide compound IV under the temperature of 80° C.-120° C. for 4-5 hours. Preferably, the organic solvent is selected from: tetrahydrofuran, ethanol, 1,4-dioxane, toluene, acetonitrile, isopropanol and n-propanol. The alkaline catalyst is an inorganic alkali or an organic alkali, wherein the inorganic alkali is selected from: sodium carbonate, sodium hydrogencarbonate, sodium hydroxide, potassium hydroxide, potassium carbonate and cesium carbonate, wherein the organic alkali is selected from: triethylamine, tripropylamine, tributylamine, N,N-dimethyl-propylamine, N,N-dimethylbenzylamine, N,N-dimethylbutylamine and N,N-diethylbutyl amine. The fluoro isatin is 5-fluoro isatin, 4-fluoro isatin, 6-fluoro-isatin or 7-fluoro isatin, preferably, the fluoro isatin is 5-fluoro-isatin. The feeding molar ratio of compound III, fluoro isatin or isatin and the triethylamine catalyst is 1:1:1-5; preferably, the feeding molar ratio is 1:1:2-3.

The substitution reaction of the step c) is usually conducted under the temperature of 80° C.-120° C. for 16-18 hours in the organic solvent and with the presence of catalysts to obtain the compound of formula I. Preferably, the organic solvent is selected from: xylene, tetrahydrofuran, 1,4-dioxane and toluene. The catalyst may be a palladium catalyst selected from: palladium acetate, palladium chloride, tetrakis (triphenylphosphine) palladium, tris(dibenzylideneacetone) dipalladium, bis (dibenzylidene acetone) palladium and [1,1'-bis (diphenylphosphino) ferrocene] dichloropalladium; or alkaline catalyst selected from: sodium carbonate, sodium hydroxide, potassium hydroxide, potassium carbonate, cesium carbonate and potassium tert-butoxide; or ligand selected from: triphenylpho sphine, 1,1'-bis(diphenylphosphino) ferrocene, 4,5-bis-diphenyl-phosphine-9,9-dimethylxanthene, 2-dicyclohexylphosphino-2',4',6'-triisopropyl biphenyl, 2-dicyclohexylphosphino-2',6'-dimethoxy biphenyl, and (±)-2,2'-bis-(diphenylphosphino)-1,1'-binaphthyl. In the step c), the feeding molar ratio of compound IV, the substrate amine compounds, the palladium catalyst, the phosphine ligand and the inorganic alkaline is 1:1-10:0.1-0.5:0.2-0.8:1-5, preferably, the feeding molar ratio is 1:2-10:0.3:0.48:2.

In another preferred embodiment, in the step c), the compound of formula IV and N-methylpiperazine, dimethylamine hydrochloride, morpholine, or piperidine are subjected to substitution reaction.

In another preferred embodiment, in the step c), the compound of formula IV and N-R'piperazine are primarily subjected to substitution reaction, wherein R' is a protection group selected from: acetyl group, propionyl group, tert-butoxycarbonyl group, benzyl group, benzyloxycarbonyl group, trityl group, trimethylsilyl group, t-butyldimethylsilyl group or a diphenylmethyl silicon group; preferably tert-butoxycarbonyl group. The substituent group of the product is removed to give the compound of formula I after the reaction steps are completed. Removal of the protection groups is conducted by common methods in the art.

The features above, or features in the embodiments can be arbitrarily combined. All features disclosed in the specification can be blended with any composition forms. Various features disclosed in the specification can be replaced by any same, equal or similar alternative features. Therefore Unless otherwise stated, the disclosed features are only equal or similar examples in general.

The main advantages of the present invention are:

(1) The present invention provides a novel N-alkyl tryptanthrin derivative.

(2) The N-alkyl tryptanthrin derivative of the present invention has a good IDO inhibitory activity.

(3) The N-alkyl tryptanthrin derivative of the present invention can be used for IDO-mediated diseases with pathological features in tryptophan metabolic pathway, thus having good potential in the development of new drugs.

(4) The preparation methods of N-alkyl tryptanthrin in the present invention can be industrialized producted.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacture's instructions. Unless indicated otherwise, parts and percentage are calculated by weight.

The present invention will be further illustrated below with reference to the specific examples. It should be understood that these examples are only to illustrate the invention but not to limit the scope of the invention. The experimental methods with no specific conditions described in the following examples are generally performed under the conventional conditions such as illustrated by Sambrook et al., in Molecular Cloning: A Laboratory Manual (New York Cold Spring Harbor Laboratory Press, 1989), or according to the manufacture's instructions. Unless indicated otherwise, parts and percentage are calculated by weight.

Unless otherwise defined, all professional and scientific terminologies are identical with terms familiar to those skilled in the art. Meanwhile, any methods and materials similar or equal to the recorded content can be acceptable methods in the present invention. The preferred examples of the methods and materials recorded hereinabove are only for demonstration purposes.

EXAMPLE 1

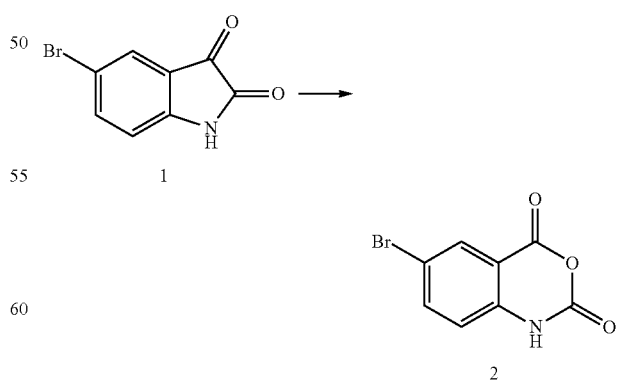

Compound 1 (500 mg, 2.2 mmol) was suspended in 10 ml of dry methylene chloride. Under 0° C., meta-chloroperoxybenzoic acid (0.76 g, 4.4 mmol, 85%) was added portion wise. The reaction mixture was stirred for 2 hours under room temperature. After the reaction was monitored as being completed by TLC (CH$_2$Cl$_2$/MeOH=50/1, Rf 0.4), the formed white solid was filtered and washed with ethyl acetate (10 ml) for three times to Rive compound 2 (420 mg, 79%).

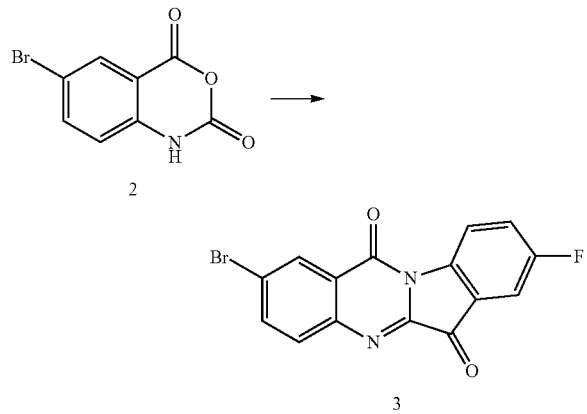

The mixture of compound 2 (3 g, 12.4 mmol), 5-fluoro isatin (2 g, 12.4 mmol) and triethylamine (3.6 ml, 24.8 mmol) was suspended in dry methylbenzene (12 ml) and was warmed under 110° C. for 4 hours. The solvent was removed under reduced pressure. The yellow solid was dissolved in dichloromethane (2 ml), and then ethyl acetate (2 ml) was added. The obtained yellow solid was filtered and washed with ethyl acetate (2 ml) for three times to give compound 3 as yellow solid (1.9 g, 44%).

$^1$H NMR (400 MHz, DMSO) δ 8.49 (s, 1H), 8.42 (d, J=9.4 Hz, 1H), 8.14 (s, 1H), 7.91 (d, J=8.6 Hz, 1H), 7.83 (s, 1H), 7.76 (s, 1H).

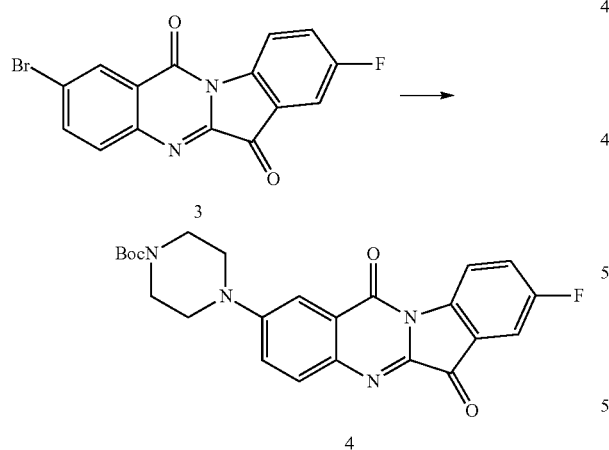

Under the protection of nitrogen, Compound 3 (100 mg, 0.29 mmol), N-Bocpiperazine (116 mg, 0.58 mmol), Pd(OAc)$_2$ (20 mg, 0.087 mmol), BINAP (84 mg, 0.14 mmol) and Cs$_2$CO$_3$ (189 mg, 0.58 mmol) were suspended in anhydrous methylbenzene (5 ml) and warmed under 110° C. for 16 hours. The reaction was monitored as completed by TLC (CH$_2$Cl$_2$/MeOH=15/1, Rf 0.4). The solvent was removed under reduced pressure. The obtained black solid was added into dichloromethane (20 ml), washed with water and saline, and dried. The concentrated black soild was separated by silicagel column (CH$_2$Cl$_2$/MeOH=15/1) to give a red solid compound 4.

$^1$H NMR (400 MHz, CDCl$_3$) δ 8.64 (dd, J=8.8, 4.1 Hz, 1H), 7.92 (d, J=9.0 Hz, 1H), 7.85 (dd, J=11.5, 8.5 Hz, 1H), 7.76 (d, J=2.9 Hz, 1H), 7.58 (dd, J=6.7, 2.6 Hz, 1H), 7.37 (dd, J=7.9, 5.2 Hz, 1H), 3.65 (m, 4H), 3.49 (m, 4H), 1.52 (s, 9H).

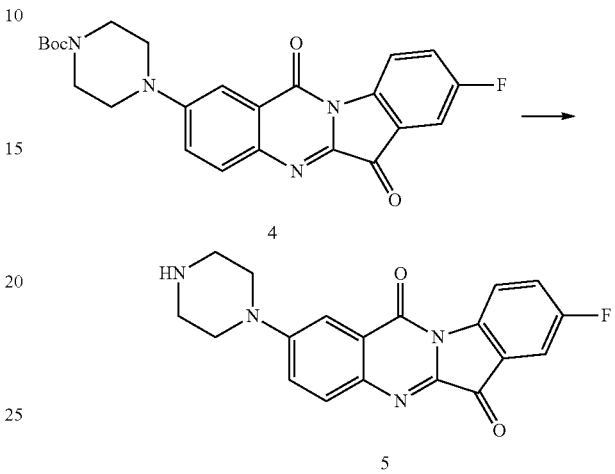

Compound 4 (50 mg, 0.11 mmol) was dissolved in dichloromethane (3 ml), and 1 ml of trifluoroacetic acid was added therein under room temperature. The reaction solution was stirred for 1 hour under room temperature. After the reaction was monitored as being completed by TLC (CH$_2$Cl$_2$/MeOH=10/1, Rf 0.2), the solvent was removed under reduced pressure. The NaHCO$_3$ protection solution (10 ml) was added. Then the solution was extracted with dichloromethane (10 ml×3). The dichloromethane phase was washed with saline, dried and concentrated. The solid concentrated was separated by silicagel column (CH$_2$Cl$_2$/MeOH=10/1) to give a yellow solid compound 5.

$^1$H NMR (400 MHz, CDCl$_3$) δ8.63 (dd, J=8.8, 4.1 Hz, 1H), 7.89 (d, J=9.1 Hz, 1H), 7.74 (d, J=2.9 Hz, 1H), 7.57 (dd, J=6.7, 2.7 Hz, 1H), 7.46 (d, J=2.7 Hz, 1H), 7.38 (dd, J=9.1, 2.9 Hz, 1H), 3.50-3.42 (m, 4H), 3.13-3.03 (m, 4H).

EXAMPLE 2

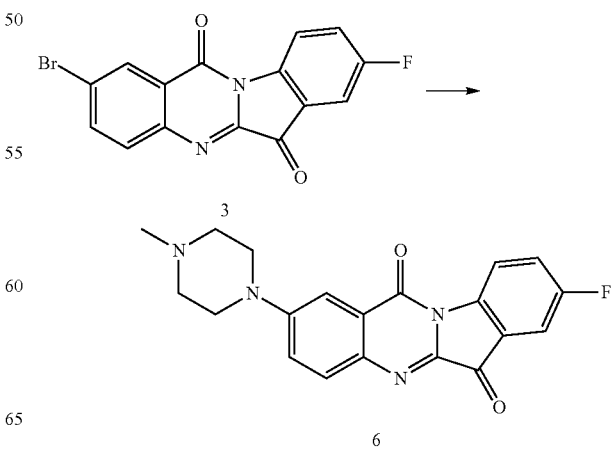

Under the protection of nitrogen, Compound 3 (100 mg, 0.29 mmol), N-Methylpiperazine (58 mg, 0.58 mmol), Pd(OAc)₂ (palladium acetate, 20 mg, 0.087 mmol), BINAP ((±)-2,2'-bis-(diphenylphosphino)-1,1'-binaphthyl, 84 mg, 0.14 mmol) and Cs₂CO₃ (189 mg, 0.58 mmol) were suspended in anhydrous methylbenzene (5 ml) and warmed under 110° C. for 16 hours. After monitored as the reaction was completed by TLC (CH₂Cl₂/MeOH=15/1, Rf 0.4), the solvent was removed under reduced pressure. Dichloromethane (20 ml) was added into the obtained black solid, washed with water and saline and dried. The black soild obtained by concentration was separated by silicagel column (CH₂Cl₂/MeOH=15/1) to give compound 6 as red solid.

¹H NMR (400 MHz, CDCl₃) δ 8.64 (dd, J=8.8, 4.1 Hz, 1H), 7.90 (d, J=9.1 Hz, 1H), 7.76 (d, J=2.9 Hz, 1H), 7.57 (dd, J=6.6, 2.7 Hz, 1H), 7.47 (td, J=8.7, 2.7 Hz, 1H), 7.39 (dd, J=9.1, 3.0 Hz, 1H), 3.57-3.43 (m, 4H), 2.69-2.57 (m, 4H), 2.40 (s, 3H).

EXAMPLE 3

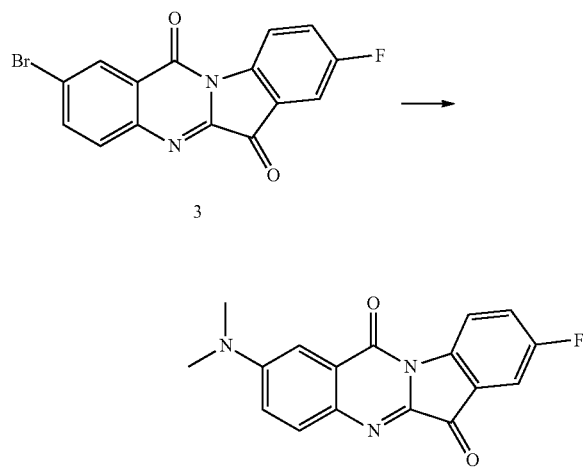

Under the protection of nitrogen, Compound 3 (100 mg, 0.29 mmol), dimethylamine hydrochloride (246 mg, 2.9 mmol), Pd(OAc)₂ (20 mg, 0.087 mmol), BINAP (84 mg, 0.14 mmol) and Cs₂CO₃ (1.1 g, 3.48 mmol) were suspended in anhydrous methylbenzene (5 ml) and warmed under 110° C. for 16 hours. After the reaction was monitored as being completed by TLC (CH₂Cl₂/MeOH=15/1, Rf 0.4), the solvent was removed under reduced pressure. The obtained black solid was added into dichloromethane (20 ml), washed with water and saline, and dried with anhydrous sodium sulfate. The black solid obtained after concentration was separated by silicagel column (CH₂Cl₂/MeOH=15/1) to give a red solid compound 7 (22 mg, 25%).

¹H NMR (400 MHz, CDCl₃) δ 8.61 (dd, J=8.8, 4.0 Hz, 1H), 7.85 (d, J=9.1 Hz, 1H), 7.55 (dd, J=6.7, 2.6 Hz, 1H), 7.50 (d, J=2.9 Hz, 1H), 7.44 (td, J=8.7, 2.6 Hz, 1H), 7.15 (dd, J=9.1, 3.0 Hz, 1H), 3.18 (s, 6H).

EXAMPLE 4

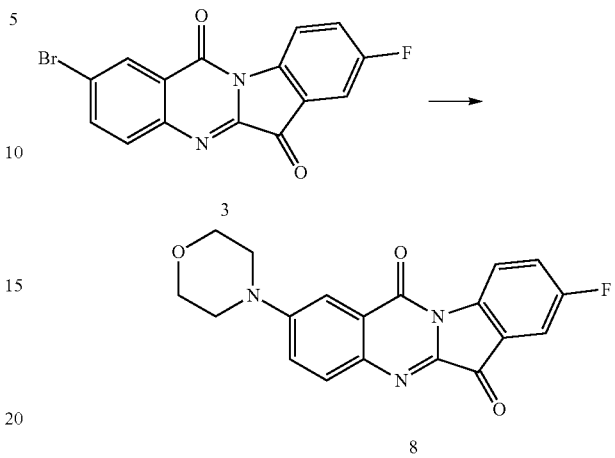

Under the protection of nitrogen, Compound 3 (100 mg, 0.29 mmol), morpholine (50 mg, 0.58 mmol), Pd(OAc)₂ (20 mg, 0.087 mmol), BINAP (84 mg, 0.14 mmol) and Cs₂CO₃ (189 mg, 0.58 mmol) were suspended in anhydrous methylbenzene (5 ml) and warmed under 110° C. for 16 hours. After the reaction was monitored as being completed by TLC (CH₂Cl₂/MeOH=15/1, Rf 0.4), the solvent was removed under reduced pressure. The obtained black solid was added into dichloromethane (20 ml), washed with water and saline, and dried, concentrated and separated by silicagel column (CH₂Cl₂/MeOH=15/1) to give compound 8 as red solid.

¹H NMR (400 MHz, CDCl₃) δ 8.65 (dd, J=8.8, 4.1 Hz, 1H), 7.93 (d, J=9.0 Hz, 1H), 7.77 (d, J=2.7 Hz, 1H), 7.61-7.55 (m, 1H), 7.48 (dd, J=9.8, 7.4 Hz, 1H), 7.39 (dd, J=9.1, 3.0 Hz, 1H), 4.00-3.77 (m, 4H), 3.54-3.29 (m, 4H).

EXAMPLE 5

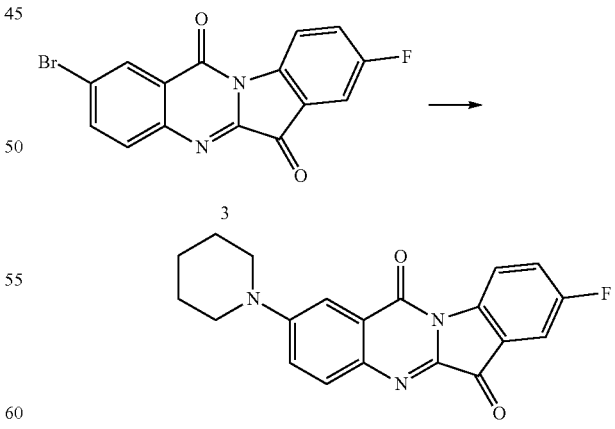

Under the protection of nitrogen, Compound 3 (100 mg, 0.29 mmol), piperidine (49 mg, 0.58 mmol), Pd(OAc)₂ (20 mg, 0.087 mmol), BINAP (84 mg, 0.14 mmol) and Cs₂CO₃ (189 mg, 0.58 mmol) were suspended in anhydrous methylbenzene (5 ml) and warmed under 110° C. for 16 hours. After the reaction was monitored as being completed by TLC (CH$_2$Cl$_2$/MeOH=15/1, Rf 0.4), the solvent was removed under reduced pressure. The obtained black solid was added into dichloromethane (20 ml), washed with water and saline, and dried. The black soild obtained by concentration was separated by silicagel column (CH$_2$Cl$_2$/MeOH=15/1) to give a red solid compound 9.

$^1$H NMR (400 MHz, CDCl$_3$) δ 8.64 (dd, J=8.6, 4.1 Hz, 1H), 7.87 (d, J=9.1 Hz, 1H), 7.74 (d, J=2.6 Hz, 1H), 7.57 (dd, J=6.7, 2.5 Hz, 1H), 7.46 (dd, J=9.8, 7.4 Hz, 1H), 7.36 (dd, J=9.1, 2.7 Hz, 1H), 3.51 (d, J=5.1 Hz, 4H), 1.74 (s, 6H).

EXAMPLE 6

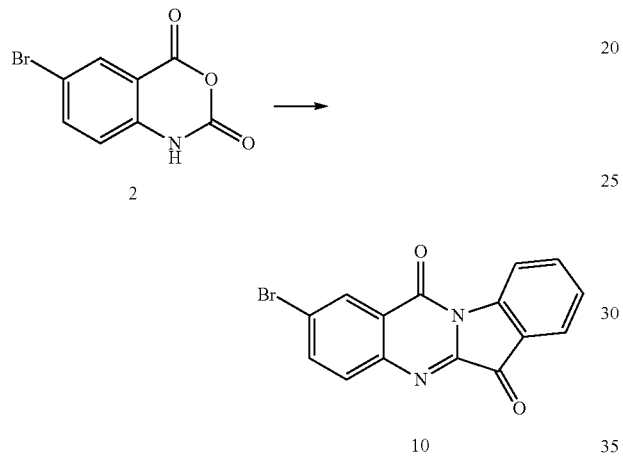

The mixture of compound 2 (1.7 g, 7.0 mmol), isatin (1.0 g, 7.0 mmol) and triethylamine (2.0 ml, 14.0 mmol) was suspended in dry methylbenzene (14 ml). The mixture was warmed under 110° C. for 4 hours. After the reaction solvent was cooled to room temperature, the obtained yellow solid was filtered and washed with ethyl acetate (2 ml) for three times to give compound 10 as yellow solid (0.5 g, 20%), which could be used directly in the next step.

Under the protection of nitrogen, Compound 10 (100 mg, 0.29 mmol), N-methyl piperazine (58 mg, 0.58 mmol), Pd(OAc)$_2$ (20 mg, 0.087 mmol), BINAP (84 mg, 0.14 mmol) and Cs$_2$CO$_3$ (189 mg, 0.58 mmol) were suspended in anhydrous methylbenzene (5 ml) and warmed under 110° C. for 16 hours. After the reaction was monitored as being completed by TLC (CH$_2$Cl$_2$/MeOH=15/1, Rf 0.4), the solvent was boiled off under hypobaric condition. The obtained black solid was added into dichloromethane (20 ml), washed with water and saline, and dried. the black solid obtained after concentration was separated by silicagel column (CH$_2$Cl$_2$/MeOH=15/1) to give a red solid compound 11 (20 mg, 20%).

$^1$HNMR (400MHz, CDCl$_3$) δ8.62 (d, J=8.1Hz, 1H), 7.90 (dd, J=8.0, 5.3 Hz, 2H), 7.81-7.71(m, 2H), 7.46-7.3 2(m, 2H), 3.56-3.40(m, 4H), 2.68-2.54(m, 4H), 2.40(s, 3 H).

EXAMPLE 7

The steps of example 7 were basically same as that of example 1, except that compound 2 was used to react with 4-fluoro isatin to give

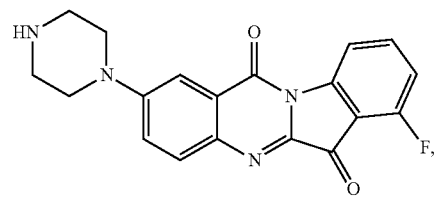 [SMILES: O=C1c2c(F)cccc2-n2c1nc1ccc(N3CCNCC3)cc1c2=O]

MS found: m/z 350.81 (M$^+$+1).

EXAMPLE 8

The steps of example 8 were basically same as that of example 1, except that compound 12 was used to react with meta-chloroperoxybenzoic acid to give compound 13.

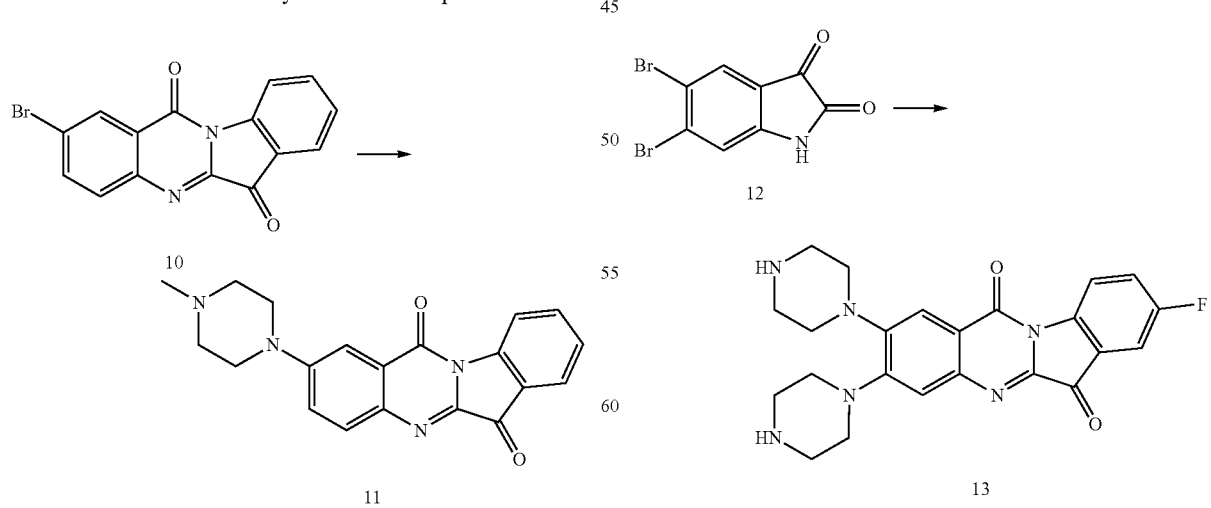

The compound 13 was detected, MS found: m/z 434.23 (M$^+$+1).

EXAMPLE 9

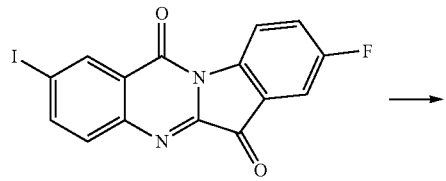

14

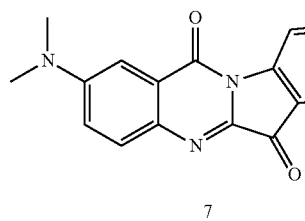

7

The steps of example 9 was basically same as that of example 3, except that compound 14 was used to react with dimethylamine hydrochloride to give compound 7.

Testing MS: m/z 309.12 (M$^+$+1).

EXAMPLE 10

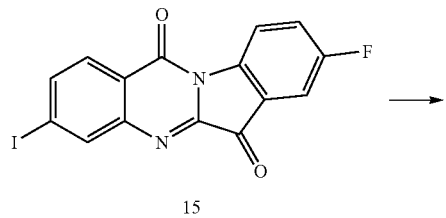

15

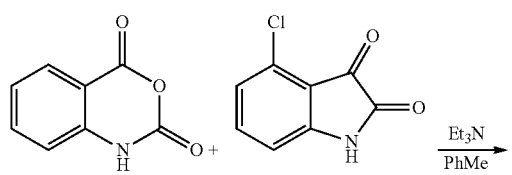

16

The steps of example 10 were basically same as that of example 3, except that: compound 15 was used to react with morpholine to give compound 16.

Testing MS: m/z 351.44 (M$^+$+1).

Comparison 1

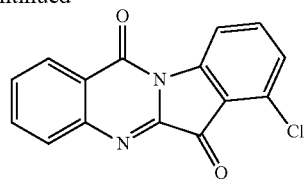

Methylbenzene (3 ml), isatoic anhydride (163 mg, 1 mmol), 4-chloroisatin (181 mg, 1 mmol, purchased from Shanghai Bangcheng Chemical Co. LTD) and triethylamine (505 mg, 5 mmol) were added into a dried round-bottom flask (25 ml), then warmed to 110° C., and stirred under reflux for 3-4 hours. After the reaction was monitored as being completed by TLC, the solvent was removed under reduced pressure. The residue was recrystallized with ethanol to obtain the desired product 7-chloro tryptanthrin (225 mg, yield 80%).

$^1$H-NMR (400MHz, CDCl$_3$) δ=8.47(d, 1H), 8.34(d, 1H), 7.95(d, 2H), 7.86(m, 1H), 7.76(m, 1H), 7.54 (m, 1H).

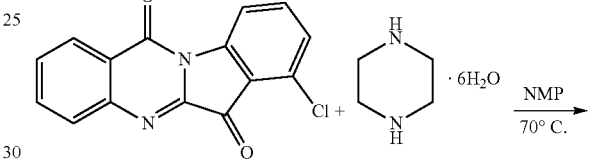

NMP (10 ml), 7-chlorine tryptanthrin (283 mg, 1 mmol), diethylenediamine and hexahydrate (252 mg, 1.3 mmol, purchased from Aladdin Co. LTD) were added into a dried round-bottom flask (25 ml), then reacted under 70° C. and the progress was tracked by TLC. After the reaction was completed, the reaction mixture was extracted with chloroform, and was purified by column chromatography isolation in which the leacheate was chloroform:methanol=95:5 to give 7-piperazine tryptanthrin (200 mg, yield 60%).

$^1$H-NMR(400MHz, CDCl$_3$) δ=6.74-8.35(m, 7H), 3.37 (t, 4H), 3.09 (m, 4H).

EXAMPLE 11

Detection of IDO Inhibitory Activity

The construction of the plasmid containing human IDO genes as well as its expression in *Escherichia Coli*, extraction and purification were conducted according to methods reported by Littlejohn et al. (Takikawa O, Kuroiwa T, Yamazaki F, et al. J. Biol. Chem. 1988, 263, 2041-2048).

IDO inhibitory activity of each compound was detected according to the following methods.

50 mM potassium phosphate buffer (pH6.5), 40 mM vitamin C, 400 μg/ml catalase, 20 μM methylene blue and IDO enzymes were mixed on a 96 well plate. Substrate L-tryptophan and the sample to be tested were added into the above-described mixture. The reaction was conducted under 37° C. for 60 minutes and was terminated by adding 30% (w/v) of trichloroacetic acid. The 96 well plate was heated under 65° C. for 15 minutes to convert the formyl kynurenine into kynurenine, and then rotated under 6000 rpm for 5 minutes. 100 μl of supernatant was taken from each well, and was transferred into a new 96-well plate. A solution of p-dimethylamino benzaldehyde in acetic acid (2% (w/v)) was added to react with kynurenine, and the yellow color caused by the reaction can be observed by Microplate Reader at 490 nm. The detection showed that the tryptamine derivatives prepared in examples 1-10 were of IDO inhibitory activity.

EXAMPLE 12

Determination of Whether the Inhibitor is Reversible

In case that the inhibitor concentration was constant, a series of enzymes of different concentrations are reacted with the inhibitor and the reaction rate was measured. The reaction rate to the enzyme concentration (v~[E]) was plotted, thus it can be determined that whether it is a reversible inhibitor according to the curve characteristics.

The reaction conduction: To 500 μl of the reaction system was added 50 mM potassium phosphate buffer (pH6.5), 40 mM vitamin C, 400 μg/ml catalase, 20 μM methylene blue, 300 mM substrate L-tryptophan and selectively 100 mM inhibitor were added. The mixture was incubated under 37° C. for 5 min, then different volumes of IDO enzymes were added. The reaction was conducted at 37° C. for 30 minutes and was terminated by adding 30% (w/v) trichloroacetic acid (200 μl). The reaction system was heated at 65° C. for 15 minutes to convert the formyl kynurenine to kynurenine, and then rotated under 12000 rpm for 10 minutes. The supernatant was taken to mix with isometric solution of p-dimethyl amidogen benzaldehyde in acetic acid (2% (w/v)). The off scale reading at 490 nm was observed using a Microplate Reader. The v~[E] was plotted. The detection showed that each tryptamine derivative prepared in examples was reversible IDO inhibitor.

EXAMPLE 13

The Determination of $IC_{50}$ (in vitro)

Firstly, 50 mM of potassium phosphate buffer (pH 6.5), 40 mM vitamin C, 400 μg/ml catalase, 20 μM methylene blue, 150 mM substrate L-tryptophan and selectively was mixed with the inhibitor. The concentrations of the inhibitors are selected as 100, 200, 400, 600, 800, 1000 and 1200 μM. The mixture was incubated for 5 minutes under 37° C., then the IDO enzyme was added into the above mixture. The reaction was conducted under 37° C. for 30 minutes and was terminated by 30% (w/v) trichloroacetic acid (200 μl). The reaction system was heated under 65° C. for 15 minutes to convert the formyl kynurenine into kynurenine, and then rotated under 12000 rpm for 10 minutes. The supernatant was taken to mix with isometric p-dimethyl amidogen benzaldehyde in acetic acid (2% (w/v)) solution. The yellow color caused by the reaction of the mixture and kynurenine, can be observed at 490 nm by using Microplate Reader. The results were calculated with $IC_{50}$ calculation software (see Table 1).

Methods in above example 12 and 13 were used for the measuring of IDO inhibitory activity of compounds prepared in examples and comparisons. 1-methyl tryptophan (1-MT, commercially available) which is the current IDO inhibitor in vitro/in vivo experiments, was used as a control. The determination results are shown in Table 1. The tryptanthrin derivatives of the present invention had better inhibitory activities when compared to the tryptanthrin derivatives of the comparison.

TABLE 1

Results of IDO Inhibitory Activies

| Under Test | Reversible Inhibitor or Not | $IC_{50}$(in vitro) μm |
|---|---|---|
| I-MT | Reversible | 380 |
| Compound 5 | Reversible | 1.19 |
| Compound 6 | Reversible | 2.20 |
| Compound 7 | Reversible | 10.35 |
| Compound 9 | Reversible | 1.80 |
| Compound 11 | Reversible | 8.01 |
| Comparison 1 | Reversible | 54.34 |

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A compound of formula (I), or a pharmaceutically acceptable salt thereof:

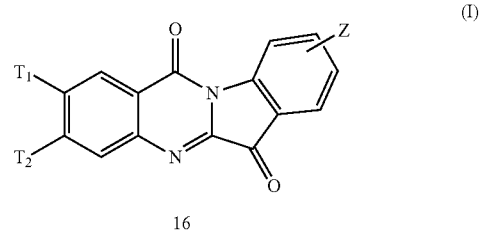

wherein Z is absent or F;
$T_1$ is

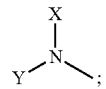

$T_2$ is H or unsubstituted $C_1$-$C_3$ alkyl

X and Y are independently substituted or unsubstituted $C_1$-$C_5$ alkyl or substituted or unsubstituted $C_1$-$C_5$ halogenated alkyl;

or X and Y are independently substituted or unsubstituted $C_1$-$C_5$ alkylene, and X and Y are linked by —$CH_2$—, —O—, or —N(Ra)—, wherein Ra is H or substituted or unsubstituted $C_1$-$C_3$ alkyl; and when a group is substituted, the substituent group is selected from the group consisting of $C_1$-$C_5$ alkyl, trifluoromethyl, and halogen.

2. The compound of formula (I) of claim 1, wherein Z is F.

3. The compound of formula (I) of claim 1, wherein X is substituted or unsubstituted $C_1$-$C_3$ alkyl; and Y is substituted or unsubstituted $C_1$-$C_3$ alkyl.

4. The compound of formula (I) of claim 1, wherein X and Y together with the adjacent N atom form the following structures:

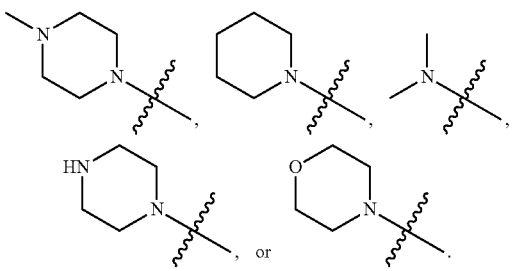

, or

5. The compound of formula (I) of claim 1, wherein the compound is:

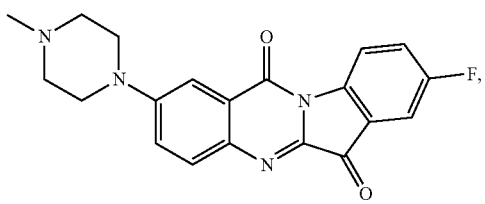

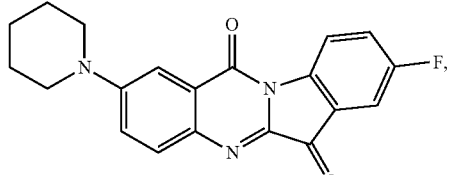

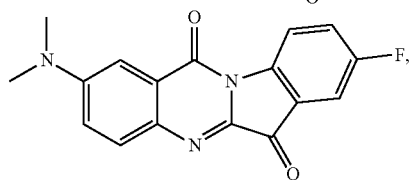

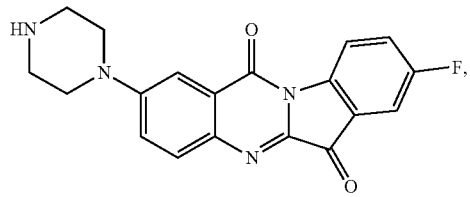

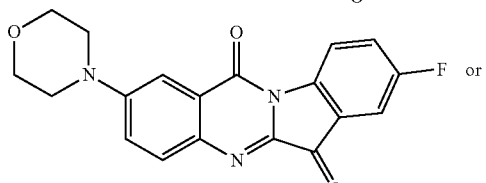

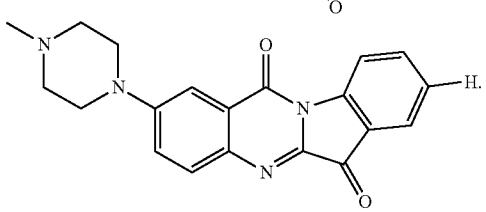

6. A preparation method for a compound of formula (I), wherein the method comprises the following steps (a)-(c):

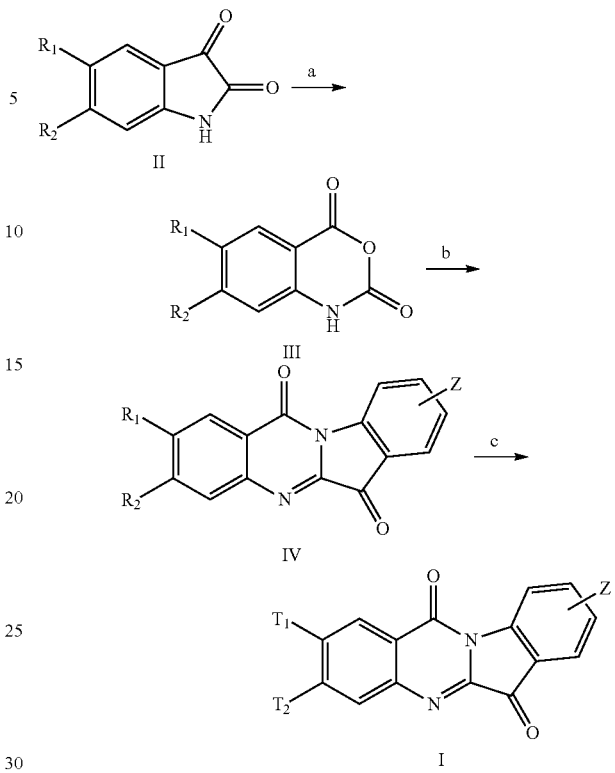

(a) oxidizing the compound of formula II to form the compound of formula III;
(b) reacting the compound of formula III with fluoric isatin or isatin thereby forming the compound of formula IV; and
(c) substituting the compound of formula IV thereby forming the compound of formula I;

wherein in each formula, $R_1$ and $R_2$ are independently selected from the group consisting of H, Br and I, provided that $R_1$ and $R_2$ are not simultaneously H;

$T_1$ is

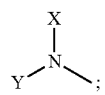

;

$T_2$ is H or unsubstituted $C_1$-$C_3$ alkyl; and
Z is absent or F.

7. A pharmaceutical composition, comprising:
the compound of formula (I) of claim 1 or a pharmaceutically acceptable salt thereof; and
a pharmaceutically acceptable carrier.

8. A method for treating a disease related to tryptophan metabolism disorder selected from the group consisting of cancer, Alzheimer's disease, cataracts, depression, anxiety disorders, AIDS, autoimmune disease, and mental disorders in a subject in need thereof, the method comprising administering to the subject the pharmaceutical composition of claim 7.

9. The method of claim 8, wherein the compound of formula (I) is:

23
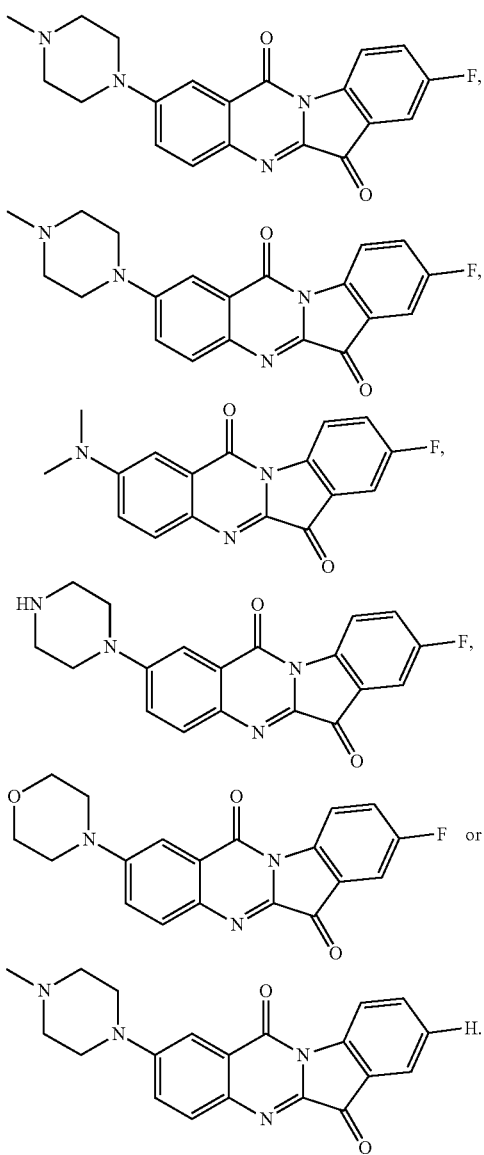
10. A method of inhibiting indoleamine 2,3-dioxygenase (IDO) activity, the method comprising contacting the compound of formula (I) of claim 1 with IDO, thereby inhibiting IDO activity.
24
11. The method of claim 10, wherein the compound of formula (I) is
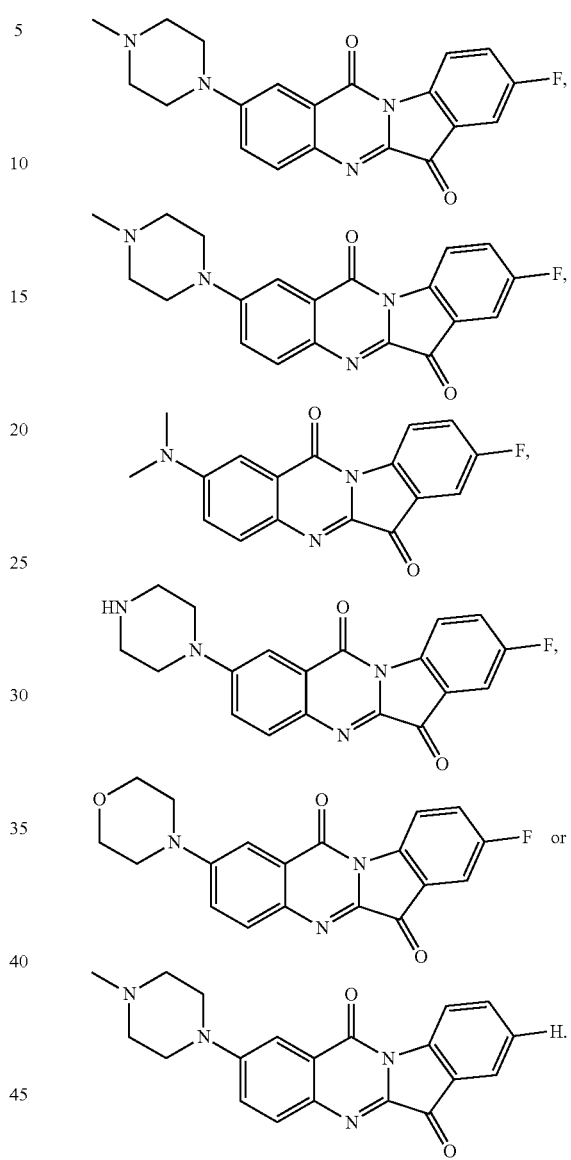
* * * * *